(12) United States Patent
Bonner, Jr. et al.

(10) Patent No.: US 6,465,473 B1
(45) Date of Patent: Oct. 15, 2002

(54) METHOD FOR TREATMENT OF REACTIVE ARTHRITIS OR BURSITIS

(76) Inventors: Ernest L. Bonner, Jr., 1406 Park St., Suite 400, Alameda, CA (US) 94501; Robert Hines, 3637 Cape Center Dr., Fayetteville, NC (US) 28304

( * ) Notice: Subject to any disclaimer, the term of this patent is extended or adjusted under 35 U.S.C. 154(b) by 0 days.

This patent is subject to a terminal disclaimer.

(21) Appl. No.: 09/510,704

(22) Filed: Feb. 22, 2000

Related U.S. Application Data

(63) Continuation-in-part of application No. 09/270,962, filed on Mar. 17, 1999, now Pat. No. 6,087,382.

(51) Int. Cl.[7] ........................ A61K 31/52; A61K 31/44; A61K 31/415; A61K 31/195
(52) U.S. Cl. ........................ 514/262; 514/356; 514/398; 514/561
(58) Field of Search ................................ 514/262, 356, 514/398, 561

(56) References Cited

U.S. PATENT DOCUMENTS 6,087,382 A * 7/2000 Bonner, Jr. et al. ......... 514/356

OTHER PUBLICATIONS

Chem. Abs. AN#1995;673023, Bunrette et al., J. Biol. Chem., 270(26), 15827–31.*

* cited by examiner

Primary Examiner—Raymond Henley, III
(74) Attorney, Agent, or Firm—Brian Beverly

(57) ABSTRACT

An improved method for treatment of conditions in human beings associated with either or both reactive arthritis or bursitis comprising administration of a combination of L-lysine, minocycline hydrochloride, metronidazole, and valacyclovir hydrochloride. A first alternate method comprises administration of L-lysine, minocycline hydrochloride, and metronidazole. A second alternate method comprises administration of L-lysine, minocycline hydrochloride, metronidazole, and isonicotinic acid hydrazide.

19 Claims, No Drawings

METHOD FOR TREATMENT OF REACTIVE ARTHRITIS OR BURSITIS

This is a continuation-in-part of application Ser. No. 09/270,962, filed Mar. 17, 1999, which is now U.S. Pat. No. 6,087,382.

BACKGROUND OF THE INVENTION

This invention relates to an improved treatment for symptoms associated in humans with reactive arthritis or idiopathic bursitis.

Reactive arthritis refers to a spondyloarthritity which usually arises as a complication of an infection elsewhere in the body. Reactive arthritis can be caused by species of Shigella bacteria (most notably *Shigella flexneri*), *Yersinia enterocolitica, Campylobacter jejuni,* several species of Salmonella, genitourinary pathogens, *Chlamydia trachomatis, Neisseria gonorrhea, Ureaplasma urealyticum, Streptococcus pyogenes,* and other yet unidentified infectious agents.

Reactive arthritis commonly occurs in young men and women, but can occur at any age. Sufferers experience joint pain, stiffness, redness or swelling. Common symptoms may include fatigue, malaise, fever, and weight loss. The joints of the lower extremities, including the knee, ankle, and joints of the foot, are the most common sites of involvement, but symptoms can also occur in the wrists, fingers, elbows, shoulders, neck, and lower back. Other symptoms may include urethritis and prostatitis in males, and cervicitis or salpingitis in females. Ocular disease is common ranging from transient, asymptomatic conjunctivitis to aggressive anterior uveitis that occasionally results in blindness. Mucocutaneous lesions and nail changes are frequent. On less frequent or rare occasions manifestations of reactive arthritis include cardiac conduction defects, aortic insufficiency, central or peripheral nervous system lesions, and pleuropulmonary infiltrates.

Treatment of patients suffering from reactive arthritis with nonsteroidal anti-inflammatory drugs ("NSAID") provides some benefit, although symptoms of reactive arthritis are rarely completely alleviated and some patients fail to respond at all. The preferred initial treatment of choice for acute reactive arthritis is indomethacin in divided doses of 75 to 150 milligrams per day. The NSAID of last resort is phenylbutazone, in doses of 100 milligrams twice or three times per day, because of its potentially serious side effects. Patients with debilitating symptoms refractory to NSAID therapy may be treated with cytotoxic agents such as azathioprine or methotrexate, or with sulfasalazine. Tendinitis, other lesions, and uveitis may benefit from corticosteroids. Minocycline hydrochloride, a semisynthetic derivative of tetracycline, is indicated for infections caused by at least Shigella microorganisms, *Streptococcus pyogenes,* and *Neisserie gonorrhoeae.* It is therefore an accepted treatment in incidents of reactive arthritis triggered by these biological entities.

Long-term follow-up studies have suggested that some joint symptoms persist in many, if not most, patients with reactive arthritis. Recurrences of the more acute symptoms are common and as many as twenty-five percent of patients either become unable to work or are forced to change occupations because of persistent joint problems.

Bursitis is inflammation of a bursa, a thin-walled sac lined with synovial tissue. The function of the bursa is to facilitate movement of tendons and muscles over bony prominences. Bursitis may be caused by excessive frictional forces, trauma, systemic disease such as rheumatoid arthritis or gout, or infection. The most common form of bursitis is subacromial. Trochanteric bursitis causes patients to experience pain over the lateral aspect of the hip and upper thigh, and tenderness over the posterior aspect of the greater trochanter. Retrocalcaneal bursitis involves the bursa located between the calcaneus and the posterior surface of the Achilles tendon. Pain is experienced at the back of the heel, and swelling appears on either or both of the medial and lateral sides of the tendon. Retrocalcaneal bursitis occurs in association with spondyloarthritities, rheumatoid arthritis, gout, and trauma.

Treatment of bursitis generally consists of prevention of the aggravating condition, rest of the involved part, an NSAID, and local steroid injection. In the long term, bursitis can result in loss of use of a joint and chronic pain syndrome.

The long term effects of reactive arthritis and bursitis range from chronic pain to crippling disability. It is also thought that many instances of osteoarthritis and psoriatic arthritis are in actuality reactive arthritis. Unfortunately, current procedures for management treat the symptoms of these diseases rather than their underlying pathogens.

SUMMARY OF THE INVENTION

The inventors have discovered that significant benefits can be obtained by treating humans affected with conditions associated with reactive arthritis or bursitis using combinations of L-lysine, minocycline hydrochloride, isonicotinic acid hydrazide (commonly referred to as InH), metronidazole, and valacyclovir hydrochloride.

L-lysine has been shown to inhibit the growth of herpes virus cultures and can be effective in alleviating the symptoms associated with herpes infections, both oral and genital.

Minocycline hydrochloride is a bacteriostatic antibiotic which exerts its antimicrobial effect by inhibition of bacterial protein synthesis. It has been shown to be effective against gram-negative bacteria, some gram-positive bacteria and other microorganisms.

InH is known to act against actively growing tubercle bacilli. Heretofore, InH has been indicated for treatment of pulmonary tuberculosis. Adults with high doses of InH sometimes are observed to have a deficiency of pyridoxine hydrochloride. Appropriate doses of pyridoxine hydrochloride are therefore administered to patients being treated with InH.

Metronidazole is an oral synthetic antiprotozoal and antibacterial agent. Heretofore it has been indicated for treatment of symptomatic trichomoniasis, intestinal amebiasis, and a wide range of intra-abdominal, skin, and gynecological, bone and joint, and lower respiratory tract and central nervous system infections, bacterial septicemia and endocarditis.

Valacyclovir hydrochloride (sold under the brand name Valtrex®) is a derivative of the anti-viral drug acyclovir. Valacyclovir hydrochloride is rapidly converted to acyclovir in the body. Acyclovir has demonstrated anti-viral activity against herpes simplex virus types I and II and varicella-zoster virus, both in vitro and in vivo.

The basic method of treatment of the invention involves administration of a combination of L-lysine, minocycline hydrochloride, and metronidazole. An alternate method includes administration of InH with the underlying combination of L-lysine, minocycline hydrochloride, and metronidazole. Another alternate method includes administration of valacyclovir hydrochloride with the underlying combination of L-lysine, minocycline hydrochloride, and metronidazole. Any of these embodiments may be supplemented with administration of pyridoxine hydrochloride, glucosamine, manganese, vitamin C, and desalinated seawater, such as Essence of Life.

The method of treatment of the invention puts the diseases of reactive arthritis and bursitis into remission. The treatment may effect a cure of reactive arthritis and bursitis, but definitive testing has not been performed to confirm that it effects a cure.

It is therefore a primary object of the invention to provide a method of treatment for conditions in human beings associated with either or both reactive arthritis or idiopathic bursitis. It is another object of the invention to provide a method for treatment of conditions in human beings associated with either or both reactive arthritis or idiopathic bursitis that puts the disease being treated into full remission.

DETAILED DESCRIPTION OF THE INVENTION

A method for treatment of the symptoms in human beings of reactive arthritis or idiopathic bursitis, or both, comprises the administration of the combination of L-lysine, minocycline hydrochloride, and metronidazole. An alternative method includes the administration of InH. The preferred method includes administration of valacyclovir hydrochloride with the underlying combination of L-lysine, minocycline hydrochloride, and metronidazole. Administration will generally be accomplished orally, but delivery could be accomplished by injection, or any other method commonly used for administration of internal medicines.

L-lysine inhibits the growth of herpes simplex viruses. The preferred dosage of L-lysine is 2 grams daily. The daily dose of L-lysine may vary from 1 to 10 grams.

The preferred dose of minocycline hydrochloride is an initial dosage of 200 mg followed by doses of 100 mg twice per day. Daily doses of minocycline hydrochloride following the initial administration of 200 mg may vary from 50 mg to 200 mg.

The preferred dose of InH in an adult is 300 mg per day and is usually reserved for those individuals who have tested positively for mycobacterial exposure. Accordingly, InH is administered only in those individuals for whom it is indicated. The daily dose of InH may vary from 50 mg to 300 mg.

The preferred dose of metronidazole is 250 mg four times per day. The total dose per day of metronidazole may vary from 100 mg to 1,000 mg.

Valacyclovir hydrochloride also inhibits herpes simplex viruses, but while L-lysine tends to stop the virus from replicating by inhibiting the initiation of the replication process, valacyclovir hydrochloride inhibits effective replication of an actively replicating viral particle by stopping replication of herpes viral DNA. This is accomplished by either competitive inhibition or inactivation of viral DNA polymerase or incorporation and termination of the growing viral DNA chain. Valacyclovir hydrochloride has never been used in the prior art for treatment of arthritis. It does not appear to be effective alone for the treatment of these diseases. The preferred dose of valacyclovir hydrochloride is 500 mg twice daily. The daily dose of valacyclovir hydrochloride may vary from 500 mg to 3 g.

The combination of minocycline hydrochloride, InH, and metronidazole inhibits the multiplication of susceptible organisms, including shigella, salmonella, chlamydia, streptococci, and mycobacteria.

The treatment method involves the combination of L-lysine, minocycline hydrochloride, and metronidazole. Where affected individuals have tested positively for mycobacterial exposure, a second treatment method includes InH in the total combination of medicines administered. The preferred embodiment of the treatment method comprises the combination of L-lysine, minocycline hydrochloride, metronidazole, and valacyclovir hydrochloride. It is believed that the addition of valacyclovir hydrochloride results in a substantial benefit due to its inhibition of virus replication. The total combination of medicines in each of these embodiments presents a broad spectrum approach that it is believed for the first time effectively addresses the underlying pathogenesis for reactive arthritis and what has previously been referred to as idiopathic bursitis, and further is a beneficial treatment for reactive arthritis in particular cases misdiagnosed as osteoarthritis or psoriatic arthritis.

EXAMPLES

The following examples serve to illustrate the invention, but are not meant to restrict the effective scope of the invention.

Example 1

An adult male presented with symptoms involving his knees, ankles, elbows, wrist and carpophalengeal joints. Stooping activities caused severe pain in his knees. Simple driving activities caused pain in his elbows, wrists, and knees. He was unable to run or jog because of pain in his knees and ankles. Lifting objects weighing more than five pounds caused wrist and hand pain. The patient was treated with metronidazole and minocycline hydrochloride for thirty days and simultaneously with L-lysine and InH for one year. Positive symptomatic relief was achieved within two weeks of treatment with the combination of metronidazole, minocycline hydrochloride, InH, and L-lysine, with complete recovery at the end of the course of treatment with InH. The patient has continued taking L-lysine because of the probable ideologic role of herpes simplex and its tendency to remain present in a dormant state. The patient now has no problems lifting, running or driving. However, it should be kept in mind that infections can reoccur and treatment with at least minocycline hydrochloride and metronidazole may be necessary again.

Example 2

A seventy-one year old female suffered from reactive arthritis and had symptoms of joint pain and stiffness involving her knees, wrists, elbows, and hips. Pain in multiple joints caused difficulty walking, arising from a sitting position to a standing position, and sitting down from a standing position. The patient was unable to run or jog. The patient was treated with metronidazole and minocycline hydrochloride for thirty days and simultaneously with L-lysine and InH for one year. Treatment effected resolution of all joint pains. After treatment the patient was able to walk without pain, to arise from a sitting position, and to sit down from a standing position without difficulty. This patient was also able to jog without discomfort or difficulty.

No adverse side effects have been observed as a result of or during the above described treatments. In the cases tested, the treatment resulted in a dramatic elimination of symptoms of the disease being addressed.

Applicants have determined that, with the contemporaneous administration of valacyclovir hydrochloride in addition to the underlying combination of L-lysine, minocycline hydrochloride, and metronidazole, arthritic patients experience substantial beneficial effects. Patients treated with the combination including valacyclovir hydrochloride were found to experience a reduction in pain and stiffness in their affected joints within approximately 48 hours, a substantially quicker response time than patients treated without valacyclovir hydrochloride included in the above combination. Further, while patients being treated with the underlying combination of L-lysine, minocycline hydrochloride, and metronidazole experienced definite beneficial effects as discussed above, some individuals were found to have residual stiffness and pain in joints, though certainly to a lesser degree than before administration of the initial combination. Patients treated with the combination including valacyclovir hydrochloride were shown to have a higher percentage of total resolution of joint stiffness and joint pain. While treatment with the combination including valacyclovir hydrochloride has been shown remarkably effective at resolution of symptoms, definitive tests have not been performed to determine if the combination effects a cure.

Individuals with severe symptoms, including joint swelling and joint contractures, who were not thought to be candidates for treatment using the combination of L-lysine, minocycline hydrochloride, and metronidazole only, have responded to treatment with that underlying combination and valacyclovir hydrochloride.

Example 3

A 46-year-old male initially presented with severe symptoms of reactive arthritis, including joint swelling and joint contractures. His symptoms had previously been diagnosed as psoriatic arthritis. His joint symptoms included pain and stiffness of multiple joints for at least five years. This individual had sausage-shaped digits on his hands and early flexion contractures at the PIP joint of those digits bilaterally. When this patient was seen initially, he had difficulty twisting lids on containers with his hands, grasping small objects, and with prolonged reaching above his head. He was also unable to run, jog, or jump. This patient was treated with a combination of L-lysine, minocycline hydrochloride, metronidazole, and valacyclovir hydrochloride. He noted a significant decrease in his pain and stiffness within 48 hours. Within one week, the joint deformities of the digits of his hands had resolved. After two weeks of treatment, he was able to run, jog, and jump. His grasping abilities significantly improved, and after one month he was able to return to work as a machinist.

Example 4

A 75-year-old female was seen with reactive arthritis previously diagnosed as osteoarthritis. Her joint problems included pain and stiffness in her shoulders, elbows, hips, hands and heels. Multiple joint pains caused her to experience difficulty walking and standing. She was initially placed on L-lysine, minocycline hydrochloride, and metronidazole. Treatment with his combination effected only minimal and transient improvement in her condition. Several months later, she returned in a semi-ambulatory state, being able to ambulate only with a walker—needing assistance to walk even with the walker. She had extreme difficulty standing from a sitting position or sitting from a standing position. She was then started on L-lysine, minocycline hydrochloride, metronidazole, and valacyclovir hydrochloride. Within 48 hours, she noted much less stiffness and much less pain in her joints. Within one month, she was able to ambulate without a walker and she noted resolution of all joint pains excepting occasional intermittent pain in her lower back.

Example 5

A 28-year-old males with reactive arthritis presented with complaints of multiple joint pain and stiffness. His symptoms caused him difficulty in raising his arms above his head, driving and bending over. Treatment was commenced with the combination of L-lysine, minocycline hydrochloride, metronidazole, and valacyclovir hydrochloride. Within 48 to 72 hours, this patient experienced significant diminution in his joint pain severity and joint stiffness. After one month of treatment, his joint pains had resolved, excepting for occasional slight pain at one shoulder. This individual's problems with raising his arms above his head, driving and bending over have resolved.

There have been thus described certain preferred embodiments of a method for treatment of conditions in human beings associated with either or both reactive arthritis or idiopathic bursitis. While preferred embodiments have been described and disclosed, it will be recognized by those with skill in the art that modifications are within the true scope and spirit of the invention. The appended claims are intended to cover all such modifications.

We claim:

1. A method for medically treating the symptoms of reactive arthritis or bursitis in humans comprising:
   administering to a patient an effective amount of the combination of L-lysine, minocycline hydrochloride, and metronidazol.

2. The treatment of claim 1 including:
   administering to a patient an effective amount of isonicotinic acid hydrazide.

3. The treatment of claim 1 including:
   administering to a patient an effective amount of valacyclovir hydrochloride.

4. The treatment of claim 3 wherein:
   (A) between approximately one and approximately ten grams per day of L-lysine are administered, (B) between approximately 50 and approximately 200 milligrams per day of minocycline hydrochloride are administered, and (C) between approximately 100 and approximately 1,000 milligrams per day of metronidazol are administered.

5. The treatment of claim 4 including:
   administration of between approximately 500 milligrams and approximately 3 grams per day of valacyclovir hydrochloride.

6. The treatment of claim 5 wherein:
   approximately one gram of L-lysine is administered once a day.

7. The treatment of claim 5 wherein:
   approximately 100 milligrams of said minocycline hydrochloride is administered twice daily.

8. The treatment of claim 5 wherein:
   approximately 250 milligrams of said metronidazol is administered four times a day.

9. The treatment of claim 5 wherein:
   approximately 500 milligrams of valacyclovir hydrochloride is administered twice daily.

10. The treatment of claim 6 wherein:
    approximately 100 milligrams of said minocycline hydrochloride is administered twice daily.

11. The treatment of claim 6 wherein:

approximately 250 milligrams of said metronidazol is administered four times a day.

12. The treatment of claim 6 wherein:

500 milligrams of valacyclovir hydrochloride is administered twice daily.

13. The treatment of claim 7 wherein:

approximately 250 milligrams of said metronidazol is administered four times a day.

14. The treatment of claim 7 wherein:

500 milligrams of valacyclovir hydrochloride is administered twice daily.

15. The treatment of claim 8 wherein:

500 milligrams of valacyclovir hydrochloride is administered twice daily.

16. The treatment of claim 10 wherein:

approximately 250 milligrams of said metronidazol is administered four times a day.

17. The treatment of claim 11 wherein:

500 milligrams of valacyclovir hydrochloride is administered twice daily.

18. The treatment of claim 11 wherein:

500 milligrams of valacyclovir hydrochloride is administered twice daily.

19. The treatment of claim 16 wherein:

500 milligrams of valacyclovir hydrochloride is administered twice daily.

* * * * *